(12) United States Patent
Roorda et al.

(10) Patent No.: US 8,852,220 B2
(45) Date of Patent: Oct. 7, 2014

(54) THROMBUS PENETRATING DEVICES, SYSTEMS, AND METHODS

(75) Inventors: Wouter E. Roorda, Palo Alto, CA (US); Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 242 days.

(21) Appl. No.: 13/227,071

(22) Filed: Sep. 7, 2011

(65) Prior Publication Data

US 2013/0060269 A1 Mar. 7, 2013

(51) Int. Cl.
*A61B 17/22* (2006.01)
*A61B 17/3207* (2006.01)
*A61B 18/04* (2006.01)
*A61B 17/00* (2006.01)

(52) U.S. Cl.
CPC .......... *A61B 17/320725* (2013.01); *A61B 2017/22094* (2013.01); *A61B 18/04* (2013.01); *A61B 2017/00867* (2013.01)
USPC .......................................... 606/159; 606/198

(58) Field of Classification Search
USPC ............ 606/127, 159, 191, 194, 198, 200; 604/95.04
See application file for complete search history.

(56) References Cited

U.S. PATENT DOCUMENTS

| 5,827,304 | A  | * | 10/1998 | Hart .............................. 606/159 |
| 6,066,149 | A  | * | 5/2000  | Samson et al. ................ 606/159 |
| 6,315,778 | B1 | * | 11/2001 | Gambale et al. ................ 606/41 |
| 6,911,026 | B1 | * | 6/2005  | Hall et al. ...................... 606/159 |
| 7,066,880 | B2 |   | 6/2006  | Wendlandt |
| 7,798,992 | B2 | * | 9/2010  | Ortiz ........................... 604/95.01 |
| 2001/0011182 | A1 | * | 8/2001 | Dubrul et al. ................ 606/200 |
| 2004/0158309 | A1 |   | 8/2004 | Wachter et al. |
| 2005/0038500 | A1 |   | 2/2005 | Boylan et al. |
| 2007/0276488 | A1 |   | 11/2007 | Wachter et al. |
| 2008/0312740 | A1 |   | 12/2008 | Wachter et al. |
| 2010/0305592 | A1 |   | 12/2010 | McGuckin, Jr. et al. |

OTHER PUBLICATIONS

DVTanswers.com, Medrad, Inc., "AngioJet Mechanical Thrombectomy", Jan. 8, 2008, www.dvtanswers.com/Treatments/thrombectomy.html.
Bacchus Vascular, "Trellis Peripheral Infusion System", Nov. 22, 2007, www.youtube.com/watch?v=aujNwoZKI_A.
EKOS Corporation, "EKOS Treatment", May 5, 2010, www.ekoscorp.com/ekostreatment.htm.
Neilkkd2000, "popliteal embolectomy, medical approach using a 4 f fogarty catheter", Apr. 21, 2009, www youtube.com/watch?v=fi3UCBOIczE.
Straub Medical AG, "Straub Mechanical Thrombectomy System", Apr. 12, 2010, http://straubmedical.com/?mid=61&tid=0&pid=52&lid=1.

* cited by examiner

Primary Examiner — Kathleen Holwerda
Assistant Examiner — Sarah W Aleman
(74) Attorney, Agent, or Firm — Workman Nydegger; Jonathan Feuchtwang

(57) ABSTRACT

A device for penetrating occlusive material in a body lumen is provided that may include an outer tube, an intermediate tube, and an inner tube. At least a portion of the intermediate tube may be moveably disposed within the outer tube. At least a portion of the inner tube may be moveably disposed within the intermediate tube. A first dynamic member may be operably connected to the intermediate tube and the inner tube. The first dynamic member may be configured to penetrate the occlusive material and to anchor the first dynamic member within the occlusive material. A second dynamic member may be operably connected to the outer tube and the intermediate tube. The second dynamic member may be configured to penetrate the occlusive material and to anchor the second dynamic member within the occlusive material and to support movement of the first dynamic member.

22 Claims, 10 Drawing Sheets

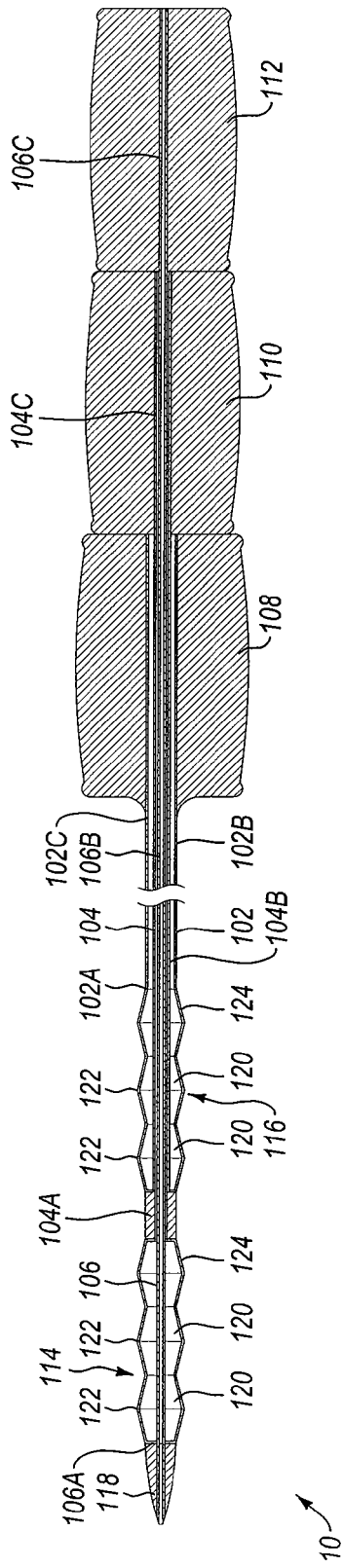
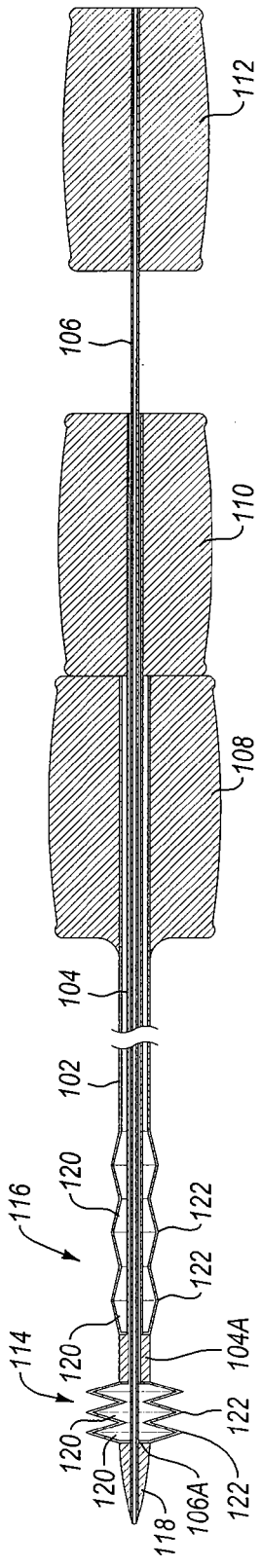
Fig. 2A
Fig. 2B

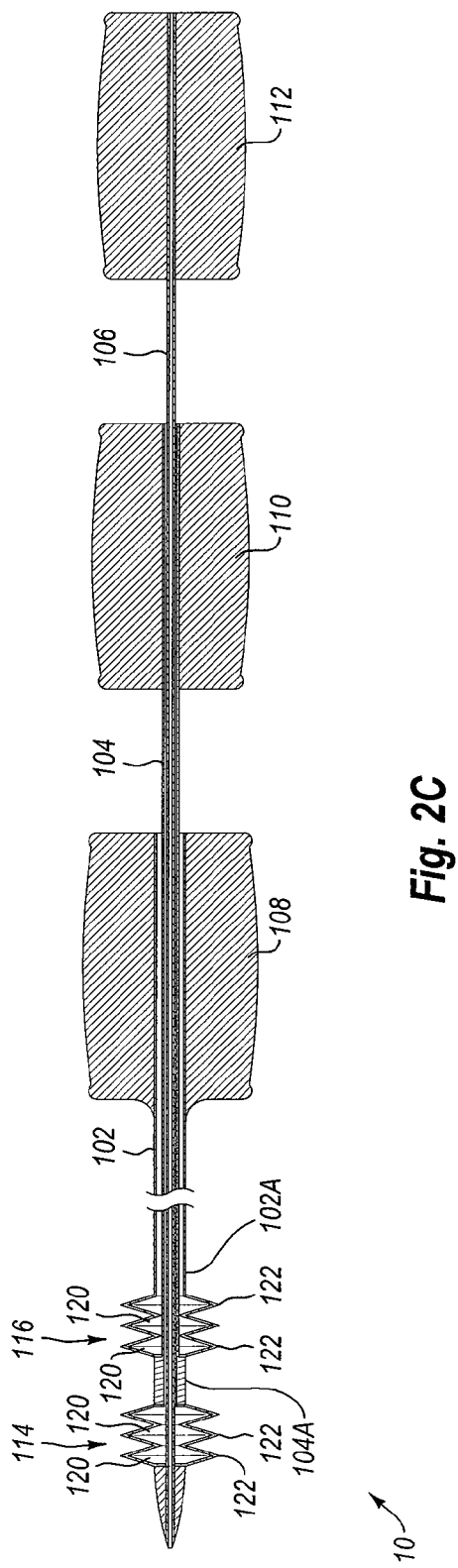
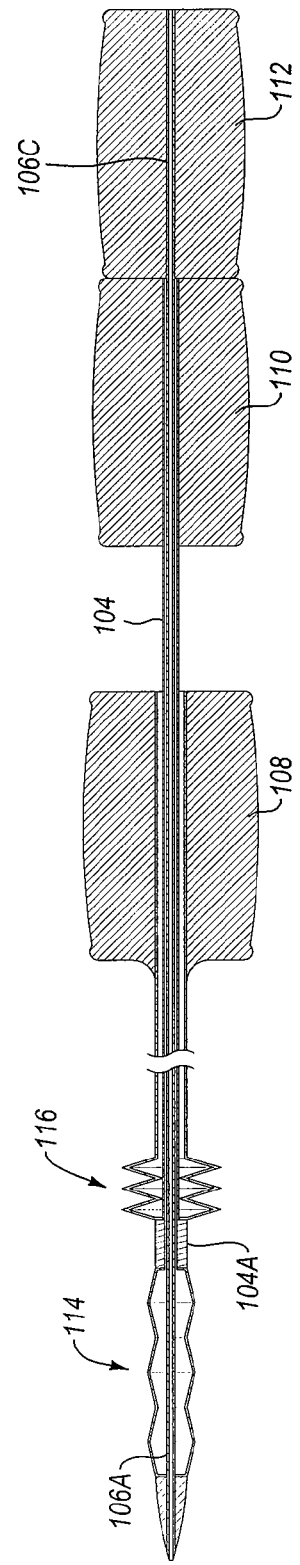
Fig. 2C
Fig. 2D

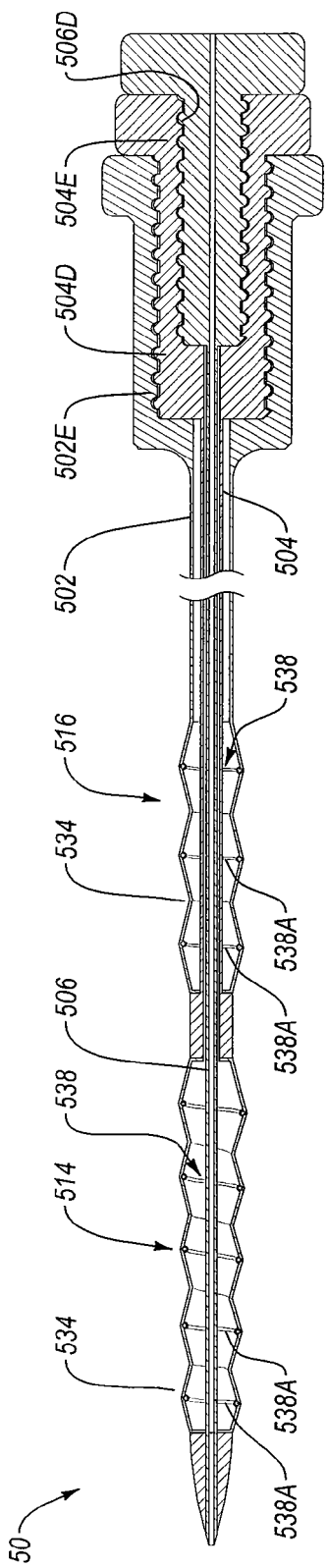
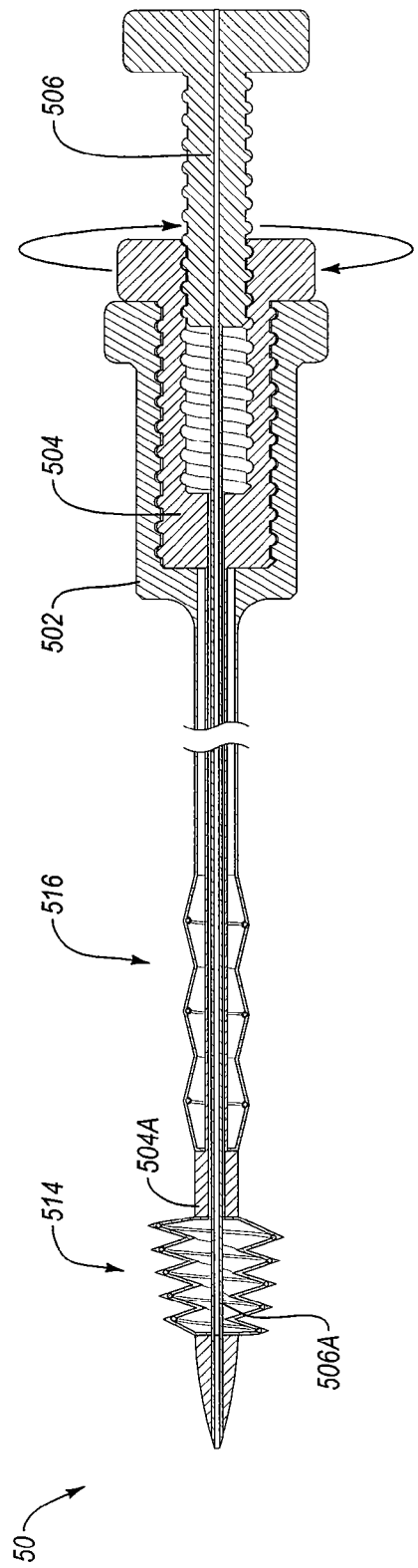
Fig. 6A
Fig. 6B

THROMBUS PENETRATING DEVICES, SYSTEMS, AND METHODS

BACKGROUND

1. Technical Field

The present disclosure relates generally to medical devices, systems, and their methods of use. In particular, the present disclosure relates to devices and systems for penetrating thrombus or other occlusive material within a body lumen, and their corresponding methods of use.

2. The Technology

The process of thrombosis may produce a fibrinous blood clot or thrombus in a patient's vasculature. Thrombus may occasionally be harmlessly dissolved in the blood stream. At other times, however, thrombus may lodge in a blood vessel or embolize to a distal blood vessel where the thrombus can partially or completely occlude the flow of blood. If the partially or completely occluded vessel provides blood to a sensitive tissue such as the brain or heart serious tissue damage or death may result. In the United States and Europe thrombosis is a leading cause of disabling diseases and death.

The occurrence and presence of thrombus can occur in several ways. Thrombus can occur in coronary procedures where thrombus is associated with myocardial infarction or heart attack. The use of vascular filters, grafts, and/or stents can also produce thrombus. Furthermore, the progression of peripheral artery disease itself can form thrombus. Venous thrombus can result from trauma, vessel injury, immobilization (i.e., bed rest), cancer, advanced age, and/or hypercoagulable blood chemistry. Thrombus can also form in arteries and other body lumens. For example, as an artery becomes blocked with atherosclerotic material, thrombus can result as blood passes through the restricted diseased artery. Finally, interventional procedures themselves can create thrombus.

Over time, thrombus can become chronic or mature, attaching to a body lumen wall and/or stiffening such that mechanical removal of the thrombus or treatment of the thrombus with thrombolytic medications becomes unacceptably difficult and/or impossible. Accordingly, treatment of chronic or mature thrombus often requires recanalization to form a new or larger flow path between the distal and proximal ends of the thrombus in order to relieve back pressure and/or restore circulation of blood or other bodily fluids within the body lumen. However, currently available systems notoriously have difficulty recanalizing chronic or mature thrombus, are difficult to use, and involve lengthy procedures.

BRIEF SUMMARY

The present disclosure relates to devices and systems for penetrating and recanalizing thrombus or other occlusive material within a body lumen, and their corresponding methods of use. In an embodiment, a device for penetrating thrombus or other occlusive material may include an outer tube, an intermediate tube, and an inner tube. At least a portion of the intermediate tube may be moveably disposed within the outer tube and at least a portion of the inner tube may be moveably disposed within the intermediate tube. The inner tube may include a penetrating member. A first dynamic member may be operably connected to the intermediate tube and the inner tube. The first dynamic member may be moveable between a first position, wherein the first dynamic member is substantially elongated to penetrate the occlusive material with a penetrating member, and a second position, wherein the first dynamic member is substantially radially expanded to anchor the first dynamic within the occlusive material. A second dynamic member may be operably connected to the intermediate tube and the outer tube. The second dynamic member may be moveable between a first position, wherein the second dynamic member is substantially elongated to penetrate the occlusive material, and a second position, wherein the second dynamic member is substantially radially expanded to anchor the second dynamic member within the occlusive material and to support movement of the first dynamic member.

In an embodiment, a device for penetrating thrombus or other occlusive material may include an outer tube, an intermediate tube, an inner tube, and an elastomeric section. At least a portion of the intermediate tube may be moveably disposed within the outer tube and at least a portion of the inner tube may be moveably disposed within the intermediate tube. The elastomeric member may surround at least a portion of the inner tube. A first dynamic member may be connected to the inner tube and the elastomeric member. The first dynamic member may be moveable between a first position, wherein the first dynamic member is substantially elongated to penetrate the occlusive material with a penetrating member, and a second position, wherein the first dynamic member is substantially radially expanded to anchor the first dynamic within the occlusive material. A second dynamic member may be connected to the outer tube and the elastomeric member. The second dynamic member may be moveable between a first position, wherein the second dynamic member is substantially elongated to penetrate the occlusive material, and a second position wherein the second dynamic member is substantially radially expanded to anchor the second dynamic member within the occlusive material and to support movement of the first dynamic member.

In an embodiment, a system for recanalizing a vessel may include a sheath having a distal end for being disposed in the vessel and a proximal end for being disposed externally to the vessel. At least a portion of a penetrating device may be moveably disposed in the sheath. The penetrating device may include an outer tube having a proximal end portion with an inner threaded portion. An intermediate tube having a proximal end portion with an outer threaded portion may be configured to engage the inner threaded portion of the outer tube. The proximal end portion of the intermediate tube may also have an inner threaded portion. An inner tube may have a proximal end portion with an outer threaded portion configured to engage the inner threaded portion of the intermediate tube. At least a portion of the inner tube may be moveably positioned within at least a portion of the intermediate tube. At least a portion of the intermediate tube may be moveably positioned within at least a portion of the outer tube. A first dynamic member may be connected to a distal portion of the intermediate tube and a distal portion of the inner tube. The first dynamic member may comprise an accordion-like structure having a plurality of segments pivotally connected to one another. The first dynamic member may be moveable between a first position, wherein the first dynamic member is substantially elongated to penetrate a thrombus, and a second position wherein the first dynamic member is substantially radially expanded to anchor the first dynamic member within the thrombus. A second dynamic member connected to the distal portion of the intermediate tube and a distal portion of the outer tube. The second dynamic member may comprise an accordion-like structure moveable between a first position, wherein the second dynamic member is substantially elongated to penetrate the thrombus, and a second position, wherein the second dynamic member is substantially radially expanded to anchor the second dynamic member within the thrombus and to selectively support movement of the first dynamic member. Finally, the device may include a penetrating member connected to the distal portion of the inner tube for penetrating the thrombus.

In an embodiment, a method for penetrating occlusive material in a body lumen with a device including a first dynamic member connected to an inner tube and an intermediate tube, the first dynamic member being movable between a penetrating position and an anchoring position, a second dynamic member connected to an outer tube and the intermediate tube, the second dynamic member being moveable between a penetrating position and an anchoring position, and a penetrating member connected to the inner tube, includes positioning the penetrating member of the device within the body lumen adjacent a proximal end of the occlusive material. The penetrating member and at least a portion of the first dynamic member may then be inserted into the proximal end of the occlusive material. The first dynamic member may then be moved into the anchoring position wherein the first dynamic member radially expands to anchor at least a portion of the first dynamic member in the occlusive material. Moving the first dynamic member into the anchoring position may also pulls at least a portion of the second dynamic member into the occlusive material. The second dynamic member may then be moved into the anchoring position to radially expand the second dynamic member and anchor at least a portion of the second dynamic member within the occlusive material. The first dynamic member may then be moved into the penetrating position to axially extend the first dynamic member and further penetrate the occlusive material with the penetrating member. The second dynamic member in the anchoring position may be configured to support movement of the first dynamic member toward the penetrating position. Finally, moving the second dynamic member between the penetrating position and the anchoring position and moving the first dynamic member between the anchoring position and the penetrating position until the penetrating member passes through a distal end of the occlusive material.

These and other advantages and features of the present disclosure will become more fully apparent from the following description and appended claims, or may be learned by the practice of the disclosure as set forth hereinafter.

BRIEF DESCRIPTION OF THE DRAWINGS

To further clarify at least some of the advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIGS. 2A-2D illustrate cross-sectional views, taken along line 2A-2A of FIG. 1, of the device shown in FIG. 1 in various configurations;

FIGS. 6A-6D illustrate cross-sectional views, taken along line 6A-6A of FIG. 5, of the device shown in FIG. 5 in various configurations.

Figure 1:
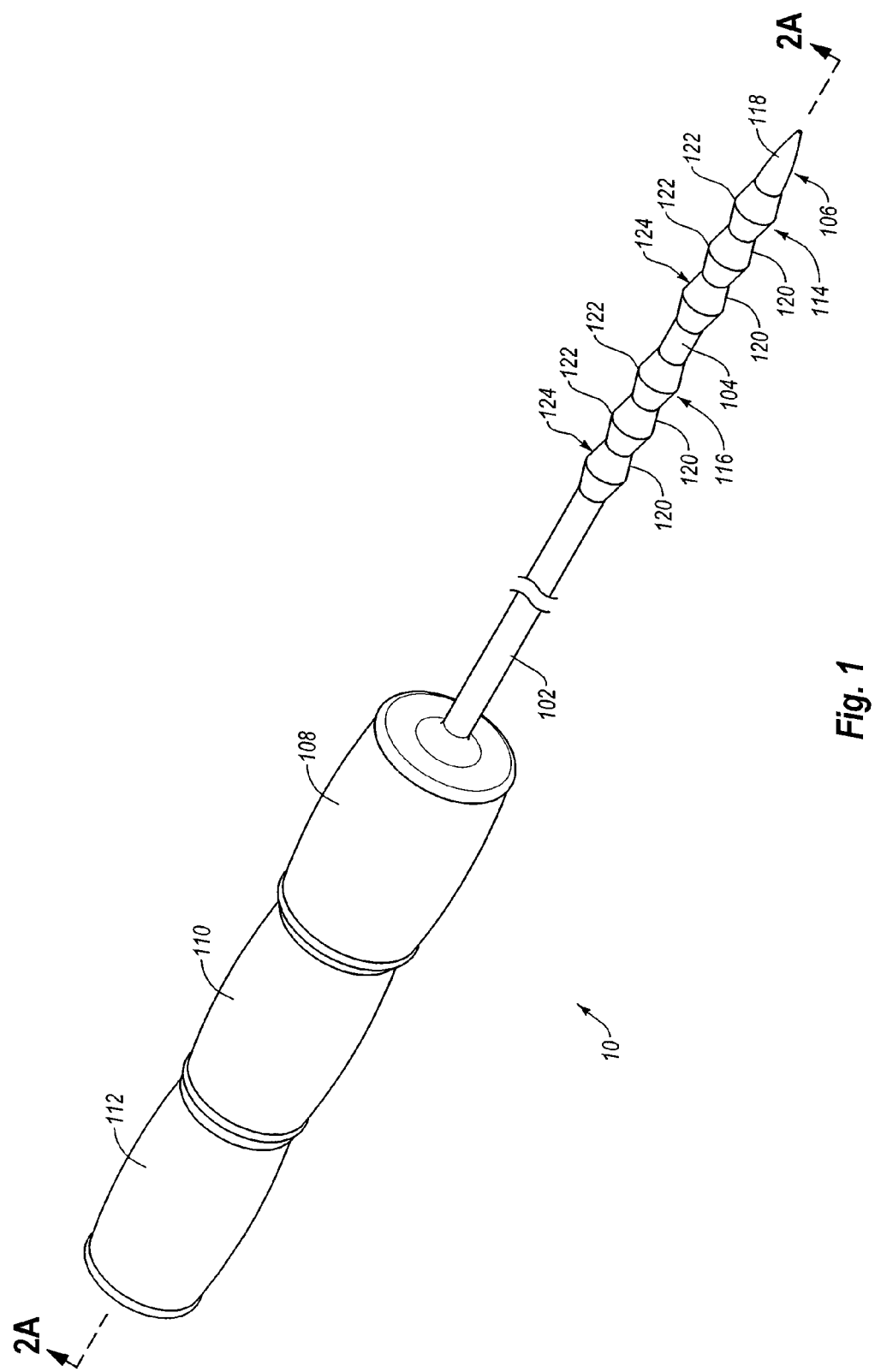
FIG. 1 illustrates a side perspective view of a device for recanalizing a vessel or penetrating thrombus according to an embodiment.

It should be noted that the figures are not drawn to scale and that elements of similar structures or functions are generally represented by like reference numerals for illustrative purposes throughout the figures. It also should be noted that the figures are only intended to facilitate the description of example configurations of the present disclosure.

DETAILED DESCRIPTION

As used herein, the term "distal" is generally defined as in the direction of the patient or away from a user of a device. In the context of a medical device intervention with or through a vessel wall, "distal" herein refers to the interior or the lumen side of the vessel wall. Conversely, "proximal" generally means away from the patient or toward the user. In the context of a medical device intervention with or through a vessel wall, "proximal" herein refers to the exterior or outer side of the vessel wall.

As used herein, the term "occlusive material" may refer to any substance or anatomic morphology that acts to severely occlude a body lumen such that it is difficult to pass bodily fluids, including blood, between the proximal end of the occlusive material to the distal end. In addition, occlusive material may make it difficult to pass medications, guide wires, catheters, devices or the like between the proximal end of the occlusive material to the distal end. Depending on the type of material occluding the body lumen (soft plaque, calcified plaque, thrombus, fibrin, clot, fatty tissue etc.) some occlusive materials may be more severe than others but all are included in the scope of the present invention when there may be some back pressure buildup or difficulty passing bodily fluids, medications, guide wires, devices, catheters, or the like through the body lumen.

As used herein, the term "recanalization" may refer to the reopening of a previously occluded passageway within a blood vessel or other body lumen.

FIG. 1 illustrates a side perspective view of a device for recanalizing a vessel or penetrating thrombus according to an embodiment. It will be appreciated that any of the devices and/or systems of the present invention can be readily adapted for use with various hollow body organs and lumens, although it may be necessary to modify the dimensions and other particular aspects of the devices and/or systems to accommodate different usage environments. In addition, it will be appreciated that any of the devices and/or systems of the present invention may be readily adapted for use with various types of occlusive materials.

As shown in FIG. 1, the device 10 may include an elongated body having an outer barrel 102, an intermediate shaft 104, an inner shaft 106 (shown in FIG. 2A), a distal handle 108, an intermediate handle 110, a proximal handle 112, a first dynamic member 114, a second dynamic member 116, and a penetrating member 118.

The elongate tubular bodies of the outer barrel 102, the intermediate shaft 104, and/or the inner shaft 106 may be flexible or may have flexible distal portions and increasingly stiffer proximal portions. The tubular bodies of the outer barrel 102, the intermediate shaft 104, and the inner shaft 106 may also have sufficient structural integrity, or "pushability," to permit the device 10 to be advanced through the vasculature and/or thrombus of a patient without buckling or undesirable kinking of the outer barrel 102, the intermediate shaft 104, and/or the inner shaft 106. The tubular bodies of the outer barrel 102, the intermediate shaft 104, and the inner shaft 106 may also be configured to transmit torque such as in those embodiments where it may be desirable to rotate the outer barrel 102, the intermediate shaft 104, and/or the inner shaft 106. The outer barrel 102, the intermediate shaft 104, and/or the inner shaft 106 may be made from a variety of materials including biocompatible materials such as a stainless steel material, polymeric material, nitinol, or other materials having the desired properties of flexibility, structural integrity, and/or torque transmission.

While the outer barrel 102, the intermediate shaft 104, and the inner shaft 106 are illustrated having cylindrical tubular bodies, the outer barrel 102, the intermediate shaft 104, and inner shaft 106 may have other cross-sectional configurations suitable to be advanced through the vasculature and/or thrombus of a patient such as an oval, rectangular, triangular cross-section, or the like. The lengths of the outer barrel 102, the intermediate shaft 104, and the inner shaft 106 may also be varied considerably to accommodate various usage environments. As shown in FIG. 1, the outer barrel 102, the intermediate shaft 104, and the inner shaft 106 may be coaxially arranged so that at least a portion of the intermediate shaft 104 may be slidably disposed within the outer barrel 102 and at least a portion of the inner shaft 106 may be slidably disposed within the intermediate shaft 104. In addition, the outer barrel 102 may be moveable relative to the intermediate shaft 104 and/or the inner shaft 106. In other embodiments, the outer barrel 102, the intermediate shaft 104, and/or the inner shaft 106 may be substantially parallel to one another. In other embodiments, the elongate tubular bodies of the outer barrel 102, the intermediate shaft 104, and/or the inner shaft 106 of the device 10 may be configured to be at least partially housed within and advanceable from a vascular access sheath (not shown). The vascular access sheath may include a distal end for being disposed in a vessel and a proximal end for being disposed externally to the vessel. The vascular access sheath may further include an elongate sheath tube formed of a flexible material which has a lumen extending therethrough and be configured to introduce the device 10 into a vessel of a patient.

The distal handle 108, the intermediate handle 110, and the proximal handle 112 may be axially aligned such that the distal handle 108, the intermediate handle 110, and the proximal handle 112 are effectively stacked one upon the other. The distal handle 108, the intermediate handle 110, and the proximal handle 112 may be configured to assist a user in gripping the device 10 and may include a textured or non slip surface, a rubber grip, a plastic grip, a neoprene grip, an ergonomically shaped grip, or any means suitable to improve the user's grip on the device 10. In other embodiments, the distal handle 108, the intermediate handle 110, or the proximal handle 112 may comprise ring segments, levers, discs, bars, or other means suitable to improve the user's grip on the device 10. In other embodiments, the distal handle 108, the intermediate handle 110, and the proximal handle 112 may be omitted and the device 10 may be sized such that the inner shaft 106 has a length greater than a length of the intermediate shaft 104 and the length of the intermediate shaft 104 may be greater than a length of the outer barrel 102. Such a configuration would allow a user to grip the inner shaft 106, the intermediate shaft 104, and/or the outer barrel 102 to manually control movement and/or operation of the device 10.

As shown in FIG. 1, the device 10 may include the penetrating member 118 connected to the inner shaft 106 (shown in FIG. 2A). The inner shaft 106 may extend through at least a portion of the penetrating member 118 (shown in FIG. 2A). Such a configuration may help secure the penetrating member 118 to the device 10. In other embodiments, the penetrating member 118 may be connected to a distal end of the inner shaft 106, an inner surface of the inner shaft 106, or any other location suitable to secure the penetrating member 118 to the device 10. The penetrating member 118 may be integrally formed on the inner shaft 106 or connected to the inner shaft 106 via adhesives, welding, an interference fit, fasteners, combinations thereof, or any other suitable technique. The penetrating member 118 may have any configuration desired such as a generally conical configuration tapering from a base to a tip as shown in FIG. 1, or a generally conical configuration terminating in a rounded or flattened tip, a screw-type configuration having helical threads, a multi-faceted configuration having two or more facets tapering from a base to a tip, or a hollow tubular needle-like configuration. In other embodiments, the penetrating member 118 may include a heating element configured to apply/transfer heat to thrombus within a vessel. Such a configuration may allow the penetrating member 118 to soften the thrombus or with heat as the penetrating member 118 penetrates. While the penetrating member 118 is shown having a lower profile than the first dynamic member 114 and the second dynamic member 116, the penetrating member 118 may have a larger profile than the first dynamic member 114 and/or the second dynamic member 116. For example, the penetrating member 118 may include a pointed tip that tapers up to a base portion that has a larger profile than the first dynamic member 114 and/or the second dynamic member 116 in one or more positions.

The first dynamic member 114 may be located between the inner shaft 106 and the intermediate shaft 104 and the second dynamic member 116 may be located between the outer barrel 102 and the intermediate shaft 104. While the first dynamic member 114 is shown being connected between the inner shaft 106 and the intermediate shaft 104 and the second dynamic member 116 is shown being connected between the outer barrel 102 and the intermediate shaft 104, the first dynamic member 114 and/or the second dynamic member 116 may be connected to and/or located on the device 10 in any suitable configuration and/or manner. For example, in an embodiment, the first dynamic member 114 may be connected to the inner shaft 106 and the intermediate shaft and the second dynamic member 116 may be connected to the first dynamic member 114 and the outer barrel 102.

As will be discussed in more detail below, the first dynamic member 114 and the second dynamic member 116 may be configured to move between anchoring and penetrating positions. Such a configuration may allow the first dynamic member 114 and the second dynamic member 116 to selectively support and/or facilitate movement of the device 10 through the thrombus in a vessel such that the device 10 may efficiently recanalize or restore blood flow through the region occupied by the thrombus with minimal damage to and/or stress on the vessel. FIG. 1 illustrates both the first dynamic member 114 and the second dynamic member 116 in the penetrating positions.

FIG. 2A illustrates a cross-sectional view, taken along line 2A-2A of the device 10 shown in FIG. 1 with the first and second dynamic members 114, 116 in the penetrating positions. As shown in FIG. 1 and FIG. 2A, the first dynamic member 114 and the second dynamic member 116 may include an accordion-like structure having a plurality of segments 120 flexibly or pivotally connected at joints, pivots, absences or hinges 122. The segments 120 and the pivots 122 may be made as separate components or can be of integral one-piece construction. The segments 120 may concentrically surround at least a portion of the inner shaft 106 and/or intermediate shaft 104 and may be rigid, semi-rigid, or otherwise structurally supportive. The segments 120 may be formed of metals, plastic, rubber (natural or synthetic), shape memory materials, any composites thereof, or other substantially rigid and durable material. Moreover, the segments 120 may be configured to have sufficient radial strength, individually or collectively, to selectively exert a predetermined force against the thrombus within the vessel without significant injury to the vessel itself.

In an embodiment, a stretchable, flexible, deformable, resilient or elastic casing 124 may be disposed over the segments 120. The casing 124 may have any desired configuration in cross-section to cover the segments 120. In other embodiments, the casing 124 may be disposed between the segments 120. The casing 124 may be made of any suitable stretchable, flexible, resilient, deformable or elastic medical grade material, such as silicone rubber or sponge, to conform or stretch to the configuration and size of the first dynamic member 114 and/or the second dynamic member 116. Optionally, the casing 124 may be omitted from the device 10.

While the first dynamic member 114 and the second dynamic member 116 are described as comprising accordion sections, the first dynamic member 114 and the second dynamic member 116 may comprise coil springs, expandable stent-like structures, wire frames, as well as inflatable membranes, or any other structure having sufficient radial strength to selectively exert a predetermined force against the thrombus within the vessel. While the first dynamic member 114 and the second dynamic member 116 are illustrated having similar structures and sizes, the first dynamic member 114 and the second dynamic member 116 may be different structures and/or sizes. For example, the first dynamic member 114 may be a reverse hour-glass shaped coil spring and the second dynamic member 116 may be an accordion section, the first dynamic member 114 may be an accordion section and the second dynamic member 116 may be an inflatable membrane, or any other combination of suitable structures. In yet another example, the second dynamic member 116 may be longer and wider than the first dynamic member 114 to provide greater anchoring of the device 10 in the thrombus as the first dynamic member 114 moves within the thrombus. In a further example, the first dynamic member 114 may have a tapered shape to assist in penetrating the thrombus while the second dynamic member 116 may have a generally cylindrical shape.

Moreover, while device 10 is illustrated having two dynamic members, device 10 may have one, three, four, five, or any number of dynamic members suitable to selectively support and/or facilitate movement of the device 10 through the thrombus in the vessel.

As shown in FIG. 2A, the outer barrel 102 may include a distal portion 102A, an intermediate portion 102B, a proximal portion 102C, and a lumen extending therethrough. The outer barrel 102 may include a larger diameter near the proximal portion 102C to help provide additional control and/or an improved grip on the outer barrel 102 and the device 10 generally. The distal handle 108 may be connected to and concentrically surround at least the proximal portion 102C of the outer barrel 102 and be configured to control movement the outer barrel 102. The distal handle 108 may be integrally formed on the outer barrel 102 or affixed to the outer barrel 102 by a suitable adhesive, welding, brazing, fasteners, soldering, or the like. The intermediate shaft 104 may be sized, shaped, and configured to be slidably disposed within at least a portion of the outer barrel 102. The intermediate shaft 104 may include a distal portion 104A, an intermediate portion 104B, and a proximal portion 104C, and a lumen extending therethrough. The intermediate shaft 104 may include a first diameter near the distal portion 104A and a second diameter near the intermediate portion 104B. The first diameter may be larger than the second diameter near the intermediate portion 104B. The first diameter near the distal portion 104A may provide a greater connection area to connect the first dynamic member 114 and the second dynamic member 116 to the intermediate shaft 104. Such a configuration may also provide the device 10 with an elongated portion having a generally uniform diameter. In other embodiments, the intermediate shaft 104 may include a constant diameter between the distal portion 104A and the proximal portion 104C. The intermediate handle 110 may be connected to and concentrically surround at least the proximal portion 104C of the intermediate shaft 104 and be configured to control movement of the intermediate shaft 104. The intermediate handle 110 may be integrally formed on the intermediate shaft 104 or affixed to the intermediate shaft 104 by any suitable method. While the intermediate handle 110 is illustrated proximal to the distal handle 108, in other embodiments the intermediate handle 110 may be distal to the distal handle 108.

Referring still to FIG. 2A, the inner shaft 106 may be sized, shaped, and configured to be slidably disposed within at least a portion of the intermediate shaft 104. The inner shaft 106 may include a distal portion 106A, an intermediate portion 106B, a proximal portion 106C, and a lumen extending therethrough. The lumen of the inner shaft 106 may extend between the penetrating member 118 and an opening formed in the proximal end of the proximal handle 112. In an embodiment, the lumen of the inner shaft 106 may be configured to remove at least portions of the thrombus from the vessel. In other embodiments, the lumen of the inner shaft 106 may be configured to deliver drugs, devices, or the like to the thrombus. In other embodiments, the lumen of the inner shaft 106 may be omitted. The proximal handle 112 may be connected to and concentrically surround at least the proximal portion 106C of the inner shaft 106 and be configured to control movement of the inner shaft 106. The proximal handle 112 may be integrally formed on the inner shaft 106 or affixed to the inner shaft 106 by any suitable method. The inner shaft 106 may include a larger diameter near the proximal portion 106C to help control and/or provide an improved grip on the inner shaft 106 and the device 10 generally.

The device 10 may also include one or more locking mechanisms (not shown). The locking mechanisms may operate to lock the axial position of the outer barrel 102, the intermediate shaft 104, and/or the inner shaft 106 relative to each other. For example, the inner shaft 106 may include a key that may be received within an axially extending guide channel on the intermediate shaft 104. The guide channel may include a number of locking slots axially spaced along an edge of the guide channel. The locking slots may be substantially perpendicular or angled relative to the longitudinal axis of the guide channel. In operation, the inner shaft 106 may be slid within the intermediate shaft 104 with the key being received in guide channel. When desired, the inner shaft 106 may be rotated in a first direction to secure the key of the inner shaft 104 within one of the corresponding locking slots thus preventing axial movement of the inner shaft 106. To move the inner shaft 106, the inner shaft 106 may be rotated in a second direction so that the key may be pulled from locking slot. The inner shaft 106 may then move axially. In other embodiments, the locking mechanism may be a compression type locking mechanism, a detent and groove type locking mechanism, a leg and guide channel type locking mechanism, a locking nut type locking mechanism, or any other suitable locking mechanism.

The penetrating member 118 may be hollow and include a lumen in communication with the lumen of the inner shaft 106 to permit transportation of drugs, devices, the thrombus, or the like between the device 10 and the vessel. In other embodiments, the penetrating member 118 may be solid and the lumen may be omitted. In other embodiments, the penetrating member 118 may include one or more perforations and/or conduits in communication with an exterior surface of the penetrating member 118 and/or the lumen of the inner shaft 106. The perforations and/or conduits of the penetrating member 118 may be configured to permit the introduction of thrombolytic agents, contrast media, or the like into the vessel and/or the thrombus through the penetrating member 118. In yet other embodiments, the perforations and/or conduits of the penetrating member 118 may be configured to permit thrombus aspiration through the penetrating member 118.

The first dynamic member 114 may include a distal end connected to the distal portion 106A of the inner shaft and a proximal end connected to the distal portion 104A of the intermediate shaft 104. The first dynamic member 114, the inner shaft 106, and the intermediate shaft 104 may be separate or can be of integral one-piece construction. The first dynamic member 114 may be connected to the inner shaft 106 and/or the intermediate shaft 104 by adhesives, welding, brazing, fasteners, soldering, or other suitable connections. In other embodiments, the connections between the first dynamic member 114 and the inner shaft 106 and/or the intermediate shaft 104 may include bearing rings or other rotatable features such that the first dynamic member 114 may rotate relative to the inner shaft 106 and/or the intermediate shaft 104. While the first dynamic member 114 is illustrated extending between the connection of the penetrating member 118 to the inner shaft 106 and the distal portion 104A of the intermediate shaft, the first dynamic member 114 may be connected the second dynamic member 116, may be connected to the intermediate portion 102B of the outer barrel 102, may enclose the penetrating member 118, or may have any other configuration suitable to move between the penetrating and anchoring positions. For example, in an embodiment, the larger first diameter portion of the distal portion 104A of the intermediate shaft 104 may be omitted and the proximal end of the first dynamic member 116 may be connected to a distal end of the second dynamic member 116 and the distal portion 104A of the intermediate shaft 104. In yet another embodiment, the larger first diameter portion of the distal portion 104A of the intermediate shaft 104 may be replaced by a ring-like connector attached to the distal portion 104A of the intermediate shaft 104. The ring-like connector may be configured to connect or directly join the distal end of the second dynamic member 116 and the proximal end of the first dynamic member 114. Such a configuration may provide for more compact movement of the first and second dynamic members 114, 116 between the penetrating and anchoring positions.

In an embodiment, the first dynamic member 114 may include one or more perforations and/or conduits in communication with an exterior surface of the first dynamic member 114 and/or the lumen of the inner shaft 106. The perforations and/or conduits of the first dynamic member 114 may be configured to permit the introduction of thrombolytic agents, contrast media, or the like into the vessel and/or the thrombus through the first dynamic member 114. In other embodiments, the perforations and/or conduits of the first dynamic member 114 may be configured to permit thrombus aspiration through the first dynamic member 114. In yet other embodiments, the perforations and/or conduits of the first dynamic member 114 may be configured to house anchoring features that can selectively extend from the perforations and/or conduits to anchor the first dynamic member 114 in the thrombus. For example, in the anchoring position, small hooks, claws, or other structures may selectively extend from the perforations and/or conduits to help anchor the first dynamic member 114 in the thrombus.

The second dynamic member 116 may have a construction and/or connections similar to the first dynamic member 114 and be may include the distal end and a proximal end. The distal end of the second dynamic member 116 may be connected to the distal portion 104A of the intermediate shaft and the proximal end of the second dynamic member 116 may be connected to the distal portion 102A of the outer barrel 102. As illustrated in FIG. 2A, the proximal end of the second dynamic member 116 may be connected to the intermediate shaft 104 at or near the region where the intermediate shaft 104 transitions between the second diameter and the first diameter. While the second dynamic member 116 is illustrated extending between the outer barrel 102 and the distal portion 104A of the intermediate shaft, the second dynamic member 116 may be connected the first dynamic member 114, may overlap the first dynamic member 114, may be connected to the inner shaft 106, or may have any configuration suitable to move between the penetrating and anchoring positions. In an embodiment, the second dynamic member 116 may include perforations and/or conduits in communication with an exterior surface of the second dynamic member 116 and/or a lumen of the intermediate shaft 104. The perforations and/or conduits of the second dynamic member 116 may be configured similar to the perforations and/or conduits of the first dynamic member 114.

In the anchoring position (shown in FIG. 2B), the segments 120 of the first dynamic member 114 may pivot relative to one another along the pivots 122 to form an angular or saw-tooth configuration with the segments 120 and at least a portion of the pivots 122 outwardly extended from the inner shaft 106 to form an enlargement or protrusion. Such a configuration may allow the first dynamic member 114 in the anchoring position to support movement of the second dynamic member 116 while minimizing the risk of damage to a vessel or vessel wall. For example, the first dynamic member 114 in the anchoring position may provide an anchor or a hold within the thrombus itself without directly pushing against the vessel wall to pull the second dynamic member 116 along with the intermediate tube 104 forward through the thrombus. Thus, the thrombus may absorb and/or distribute the majority of stresses created by the first dynamic member 114 in the anchoring position rather than the vessel wall. In addition, risk of the first dynamic member 114 inadvertently puncturing through the vessel wall is significantly reduced because the thrombus may provide a protective barrier between the first dynamic member 114 and the vessel wall. In the penetrating position (shown in FIG. 2A), the segments 120 of the first dynamic member 114 may be substantially longitudinally axially or substantially parallel or in alignment with the longitudinal axis of the inner shaft 106. The penetrating position of the first dynamic member 114 may allow the inner shaft 106 to safely move the first dynamic member 114 and the penetrating member 118 through the thrombus without slicing or other potentially damaging actions to the vessel wall. Moreover, the first dynamic member 114 and the penetrating member 118 may be advanced through the thrombus in a relatively short amount of time because of the reduced risk of damaging the vessel wall.

Similar to the first dynamic member 114, the second dynamic member 116 in the anchoring position (shown in FIG. 2C) may have the segments 120 pivoted relative to one another along the pivots 122 to form an enlargement or protrusion. The anchoring position of the second dynamic member 116 may allow the second dynamic member 116 to support movement of the first dynamic member 114. For example, the second dynamic member 116 in the anchoring position may provide an anchor or support for the inner shaft 106 to move the first dynamic member 114 forward through the thrombus Like the first dynamic member 114, the second dynamic member 116 may support safe and efficient movement of the first dynamic member 114 through the thrombus with minimized risk of damaging the vessel wall. In the penetrating position (shown in FIG. 2A), the segments 120 of the second dynamic member 116 may be substantially parallel or in alignment with the longitudinal axis of the intermediate shaft 104. The penetrating position of the second dynamic member 116 may allow the intermediate shaft 104 and/or the first dynamic member 114 to move the second dynamic member 116 through the thrombus with little or no harm to the vessel wall.

The amount of radial expansion and axial contraction of the first dynamic member 114 and the second dynamic member 116 may vary based on the configuration of the first dynamic member 114 and the second dynamic member 116 and/or the composition of the thrombus 610. For example, the second dynamic member 116 may have a radial dimension in the anchoring position that is greater than a radial dimension of the first dynamic member 114 in the anchoring position.

FIGS. 2A-2D will now be referenced to describe movement of both the first dynamic member 114 and the second dynamic member 116 between the penetrating and anchoring positions. As shown in FIG. 2A, the first dynamic member 114 may be in the penetrating position when intermediate handle 110 and the proximal handle 112 are positioned together. As also shown in FIG. 2A, the second dynamic member 116 may be in the penetrating position when the distal handle 108 and the intermediate handle 110 are positioned together.

As shown in FIG. 2B, the first dynamic member 114 may move toward the anchoring position when the intermediate handle 110 and the proximal handle 112 are moved apart. In the illustrated embodiment, the intermediate handle 110 may be moved distally relative to the proximal handle 112 to move the distal portion 104A of the intermediate shaft 104 toward the distal portion 106A of the inner shaft 106. Consequently, the intermediate shaft 104 moves the first dynamic member 114 into the anchoring position. In other embodiments, the proximal handle 112 may be moved proximally relative to the intermediate handle 110 to move the first dynamic member 114 toward the anchoring position. Depending on the direction of movement (i.e., distal or proximal) of the first dynamic member 114, the penetrating member 118 or the distal portion 104A of the intermediate shaft 104 may provide a stop or support to move the first dynamic member 114 into the anchoring position.

The amount of axial movement between the outer barrel 102, the inner shaft 106, and/or the intermediate shaft 104 may be defined by the dimensional relationships of the handles, the outer barrel, the intermediate shaft, the inner shaft, and the dynamic members in the penetrating and anchoring positions. For example, the amount of axial movement between the inner shaft 106 and the intermediate shaft 104 may be defined by the length of a portion of the inner shaft 106 between a distal end of the proximal handle 112 and a proximal end of the intermediate handle 110.

As shown in FIG. 2C, the second dynamic member 116 may move toward the anchoring position when the distal handle 108 and the intermediate handle 110 are moved apart. In the illustrated embodiment, the distal handle 108 may be moved distally relative to the intermediate handle 110 to move the distal portion 102A of the outer barrel 102 toward the distal portion 104A of the intermediate shaft 104. As a result, the outer barrel 102 moves the second dynamic member 116 into the anchoring position. In other embodiments, the intermediate handle 110 may be moved proximally relative to the distal handle 108 to move the second dynamic member 116 toward the anchoring position. Depending on the direction of movement (i.e., distal or proximal) of the second dynamic member 116, the distal portion 104A of the intermediate shaft 104 or the distal portion 102A of the outer barrel 102 may provide a stop or a backing to move the second dynamic member 116 into the anchoring position. Relative axial movement between the outer barrel 102 and the intermediate shaft 104 may be defined by a length of the intermediate shaft 104 between a distal end of the proximal handle 112 and a proximal end of the intermediate handle 110, an axial length of the second dynamic member 116 in the penetrating position, or other dimensional relationships of the device 10.

As shown in FIG. 2D, the first dynamic member 114 may move from the anchoring position toward the penetrating position when the intermediate handle 110 and the proximal handle 112 are moved back together. In the illustrated embodiment, the proximal handle 112 may be moved distally relative to the intermediate handle 110 to move the distal portion 106A of the inner shaft 106 away from the distal portion 104A of the intermediate shaft 104. As a result, the inner shaft 106 moves the first dynamic member 114 into the penetrating position. In other embodiments, the intermediate handle 110 may be moved proximally relative to the proximal handle 112 to move the first dynamic member 114 toward the penetrating position.

The second dynamic member 116 may also move from the anchoring position toward the penetrating position when the intermediate handle 110 and the distal handle 108 are moved back together.

As illustrated above, according to an embodiment, the first dynamic member 114 may be in the anchoring position when the proximal handle 112 and the intermediate handle 110 are positioned apart and the first dynamic member 114 may be in the penetrating position when the proximal handle 112 and the intermediate handle 110 are positioned together. Similarly, the second dynamic member 116 may be in the anchoring position when the intermediate handle 110 and the distal handle 108 are positioned apart and the second dynamic member 116 may be in the penetrating position when the intermediate handle 110 and the distal handle 108 are positioned together.

Figure 3:
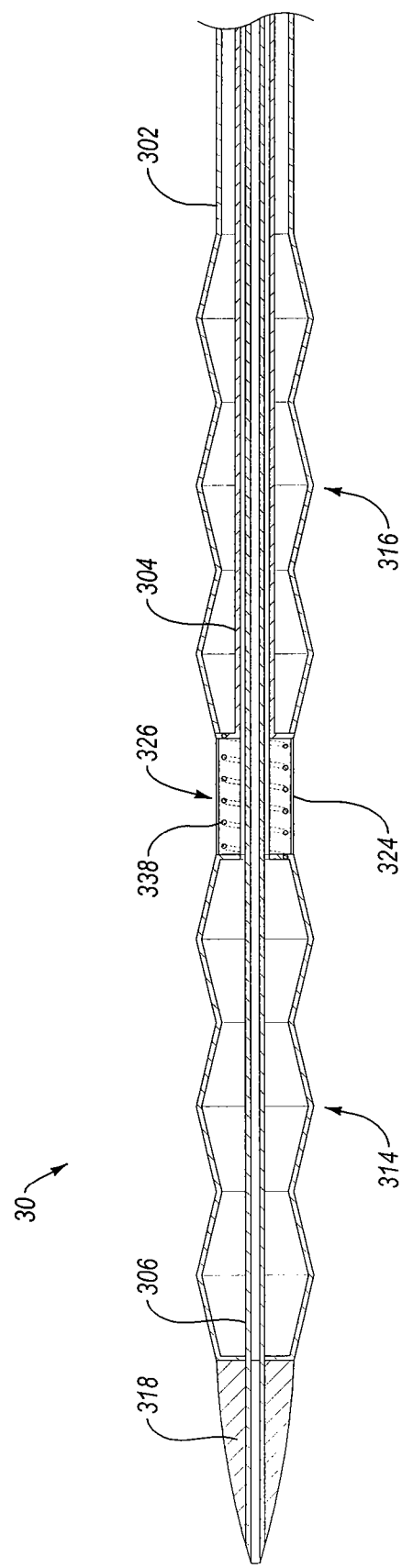
FIG. 3 illustrates a partial cross sectional view of a device for recanalizing a vessel or penetrating thrombus according to an embodiment.

While movement of the first dynamic member 118 and the second dynamic member 120 between the penetrating and anchoring positions have been described with reference to axial movement and positions of the handles 108, 110, and 112, any type of movement that results in desired movement of the first dynamic member 114 and/or the second dynamic member 116 is possible. For example, the handles 108, 110, and 112 may be omitted and other suitable members, mechanisms, and/or methods may be used to move the first dynamic member 114 and the second dynamic member 116 between the penetrating and anchoring positions. Moreover, while the first dynamic member 114 and the second dynamic member 116 are illustrated being moved manually, the first dynamic member 114 and the second dynamic member 116 may move automatically or without the need of a physical actuator. For example, FIG. 3 illustrates a partial cross sectional view of a device 30 for penetrating thrombus within a vessel.

The device 30 may be similar in many respects to device 10, except that a spring or elastomeric section 326 may be connected between the dynamic members rather than the distal portion of the intermediate shaft. Specifically, a first dynamic member 314 may be connected to an inner shaft 306 and a distal end of the elastomeric section 326. A second dynamic member 316 may be connected to an outer barrel 302 and/or an intermediate shaft 304 and a proximal end of the elastomeric section 326. The elastomeric section 326 may include a casing 324 surrounding a spring 338. Such a configuration may allow the elastomeric section 326 to cause the first dynamic member 314 and the second dynamic member 316 to mechanically lag movement of one another. In an embodiment, the second dynamic member 316 may compress the elastomeric section 326 from a resting position to a contracted position as the second dynamic member 316 moves from the penetrating position to the anchoring position. As the elastomeric section 326 expands to move back towards its resting position, the stored energy in the elastomeric section 326 may push the first dynamic member 314 toward the anchoring position from the penetrating position. In yet another example, when the first dynamic member 314 moves from the anchoring position to the penetrating position, the first dynamic member 314 may stretch or pull the elastomeric section 326 from the resting position toward an elongated position. As the elastomeric section 326 contracts to return toward its resting configuration, the stored energy in the elastomeric section 326 may pull the second dynamic member 316 towards the penetrating position from the anchoring position. Accordingly, the elastomeric section 326 may cause the first dynamic member 314 and/or the second dynamic member 316 to move between the penetrating and anchoring positions without manual actuation from a handle, tube, shaft, or other member.

FIGS. 4A-4E are partial cross sectional views illustrating exemplary steps in a method of penetrating thrombus and/or recanalizing a vessel with the device 10. For ease of reference, only the distal portion of the device 10 is shown and described. While the method is illustrated using device 10, it will be appreciated that the described method may utilize device 30 or any other device or system disclosed herein. It will also be appreciated that the first driver device 114 and the second driver device 116 may be controlled and/or moved in a similar manner as described above with reference to FIGS. 1-3.

Figure 4A:
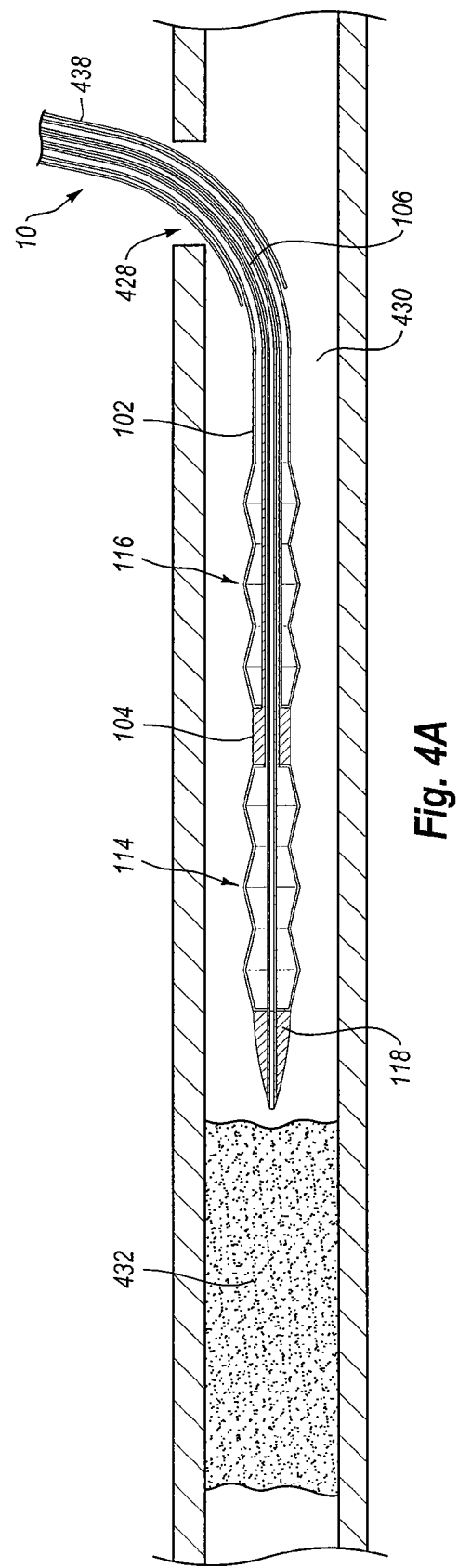
FIGS. 4A-4E are partial cross sectional views illustrating exemplary steps in a method of penetrating thrombus and/or recanalizing a vessel.

Referring now to FIG. 4A, the method can begin by inserting a vascular access sheath 438 through an access tract 428 in a vessel 430. The device 10 may then be advanced through the access tract 428 and positioned within the vessel 430 with the penetrating member 118 adjacent a thrombus 432. While the vessel 430 is illustrated being completely blocked by the thrombus 432, it will be appreciated that the thrombus 432 may be also be substantially, or partially blocking blood flow through the vessel 430 and the device 10 may be used to expand any pre-existing flow path through the thrombus 432 in order to relieve back-pressure that may be present in the vessel 430. As shown, the first dynamic member 114 and the second dynamic member 116 may be in the penetrating positions. While the method is illustrated as beginning with the first dynamic member 114 and the second dynamic member 116 in the penetrating positions, the method can begin with the first dynamic member 114 and the second dynamic member 116 in any position. In other embodiments, insertion of the vascular access sheath 438 into the access tract 428 may be omitted.

Figure 4B:
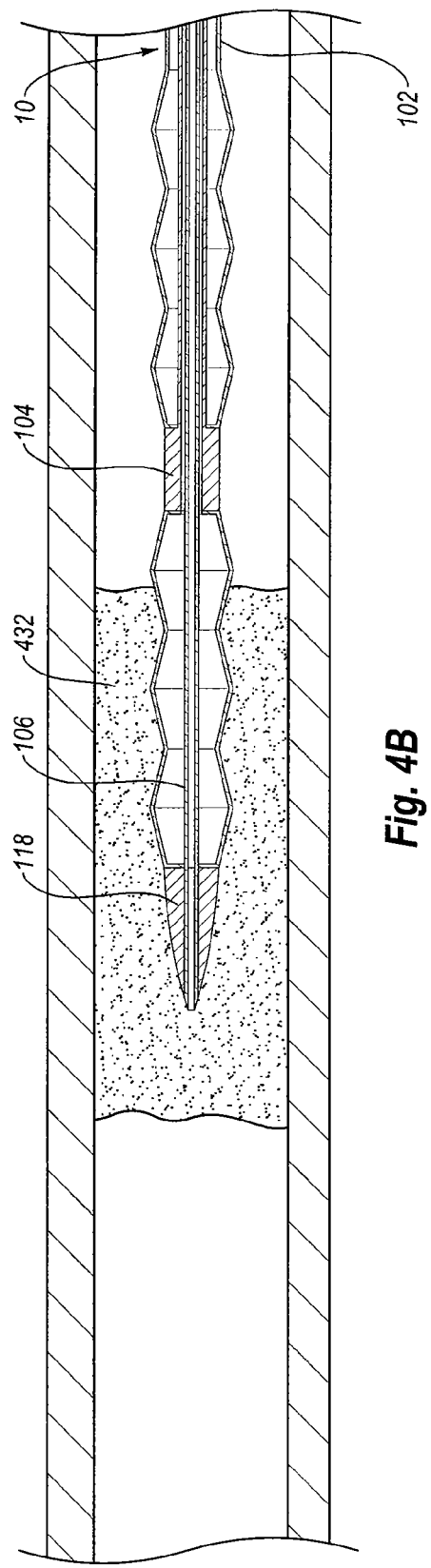

With the penetrating member 118 adjacent the thrombus 432, the device 10 may be advanced distally to insert the penetrating member 118 within the thrombus 432 as shown in FIG. 4B. Insertion of the penetrating member 118 within the thrombus 432 may be accomplished by advancing the full device 10 distally or the inner shaft 106 distally.

Figure 4C:
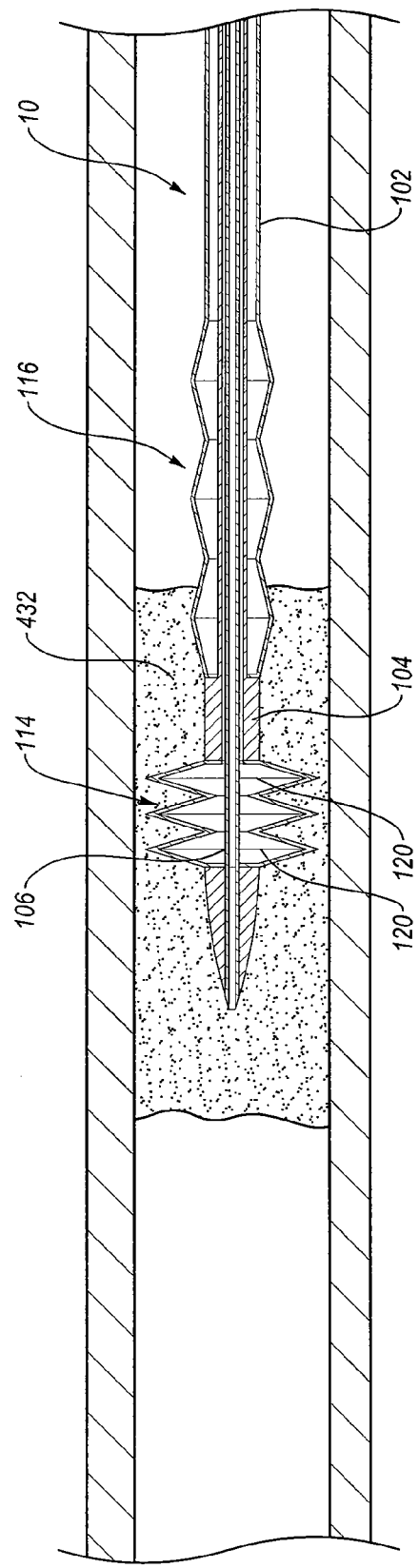

As shown in FIG. 4C, the first dynamic member 114 may be moved to the anchoring position to cause the segments 120 to radially expand away from the inner shaft 106 and to contract the segments 120 axially toward the distal end of the first dynamic member 114. The radial expansion of the first dynamic member 114 may substantially anchor the first dynamic member 114 in the thrombus 432 by forcing the segments 120 of the first dynamic member 114 radially into the thrombus 432. In addition, the associated axial contraction of the first dynamic member 114 may pull at least a portion of the intermediate shaft 104 and/or the second dynamic member 116 through the proximal end of the thrombus 432. The distance between the proximal end of the first dynamic member 114 and the distal end of the second dynamic member 116 and/or the distance the first dynamic member 114 axially contracts may be pre-selected based on how much penetration of the second dynamic member 116 into the thrombus 432 is desired as a result of movement of the first dynamic member 114 into the anchoring position.

Figure 4D:
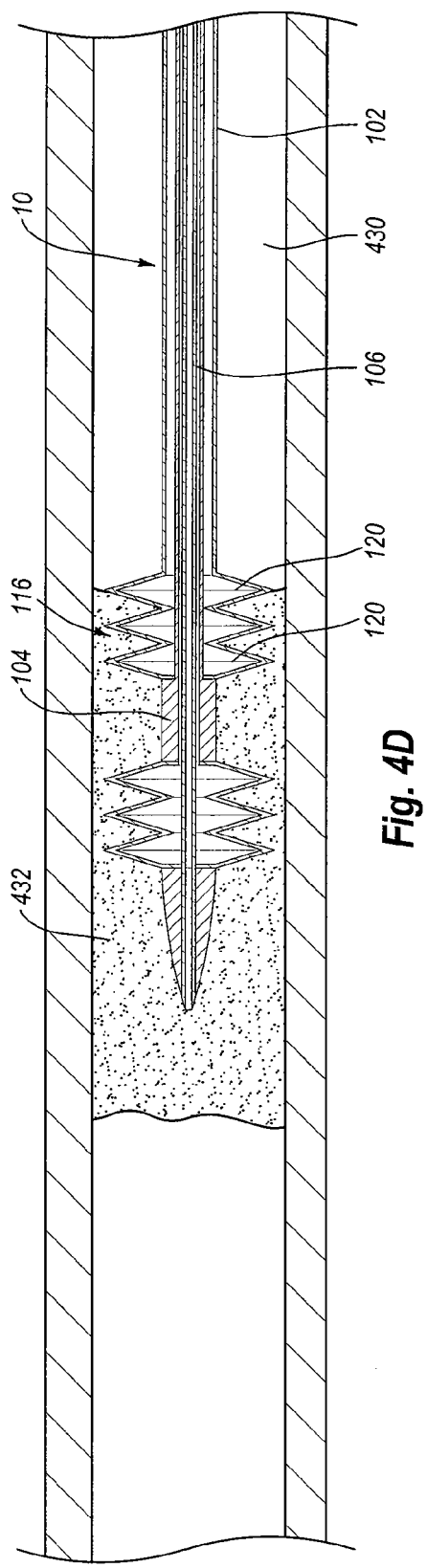

Thereafter, the second dynamic member 116 may be moved to the anchoring position to cause the segments 120 of the second dynamic member 116 to radially expand away from the intermediate shaft 104 and to contract axially toward the distal end of the second dynamic member 116 as shown in FIG. 4D. The second dynamic member 116 may substantially anchor itself in the thrombus 432 by forcing the segments 120 of the second dynamic member 116 into the body of the thrombus 432. Movement of the second dynamic member 116 into the anchoring position also axially contracts the second dynamic member 116 such that a substantial portion of the second driver 116 may pull itself into the thrombus 432.

Figure 4E:
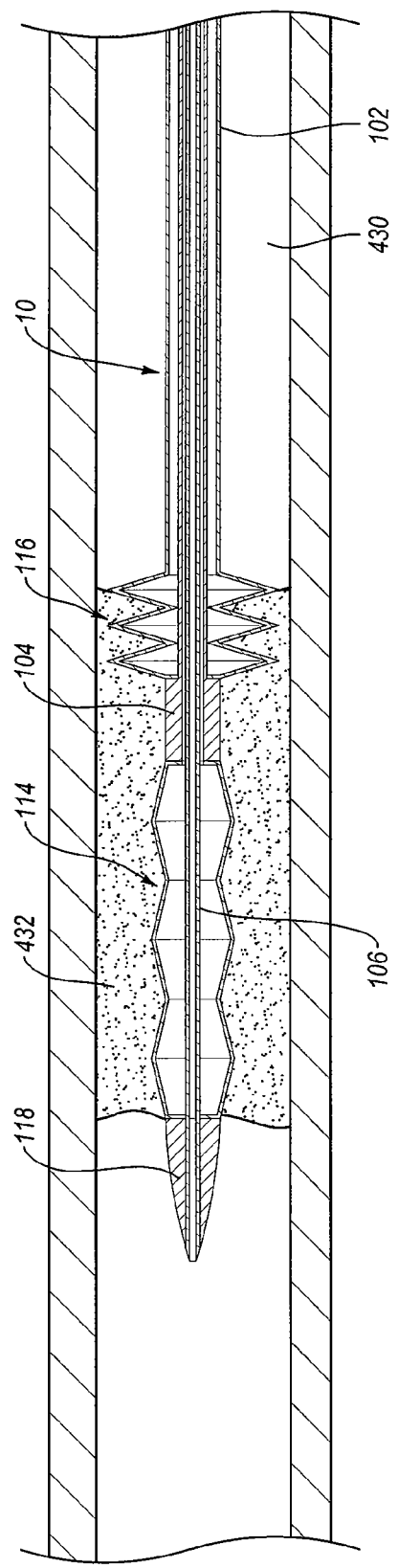

Finally, with the second dynamic member 116 substantially anchored in the thrombus 432, the first anchoring portion 114 may be moved to the penetrating position as shown in FIG. 4E. The second dynamic member 116 in the anchoring position may provide a support or anchor to move the first dynamic member 114 and the penetrating member 118 forward through the distal end of the thrombus 432 without causing undue stress or damage to the vessel 430 proximate the thrombus 432. With the device 10 extending through the proximal end and the distal end of the thrombus 432, the thrombus 432 can be considered fully penetrated and recanalized. Such an embodiment provides a fast and uncomplicated method to recanalize a vessel containing a mature thrombus with any of the devices or systems disclosed herein.

In another embodiment, with the thrombus 432 fully penetrated and recanalized, the device 10 may be removed from the vessel 430 and a stent (not shown) may be inserted through the tract of the device 10 in the thrombus 432 to maintain blood flow through the region occupied by the thrombus 432. In other embodiments, a guide wire may be passed through the thrombus 432 via the lumen of the inner shaft 106 and the penetrating member 118 to guide the placement of the stent. In other embodiments, the tract left by the device 10 in the thrombus 432 or the lumen of the inner shaft 106 of the device 10 may be used to pass thrombolytic medications, guidewires, or other items through or into the thrombus 432.

The number of steps in the method described may be varied depending on the length of the thrombus 432. For example, where the thrombus 432 has a length greater than the length illustrated in FIGS. 4A-4E, the steps describing the movement of the first dynamic member 114 and the second dynamic member 116 between the penetrating and anchoring positions may be repeated until the penetrating member 118 passes through the distal end of the thrombus 432. In other embodiments, where it is desired to pass both the first dynamic member 114 and the second dynamic member 116 through the distal end of the thrombus 432, the steps describing the movement of the first dynamic member 114 and the second dynamic member 116 between the penetrating and anchoring positions may be repeated until the second dynamic member 116 passes through the distal end of the thrombus 432.

Accordingly, as shown in FIGS. 4A-4E the device 10 and other devices described herein may be configured to penetrate and recanalize thrombus within a vessel.

Figure 5:
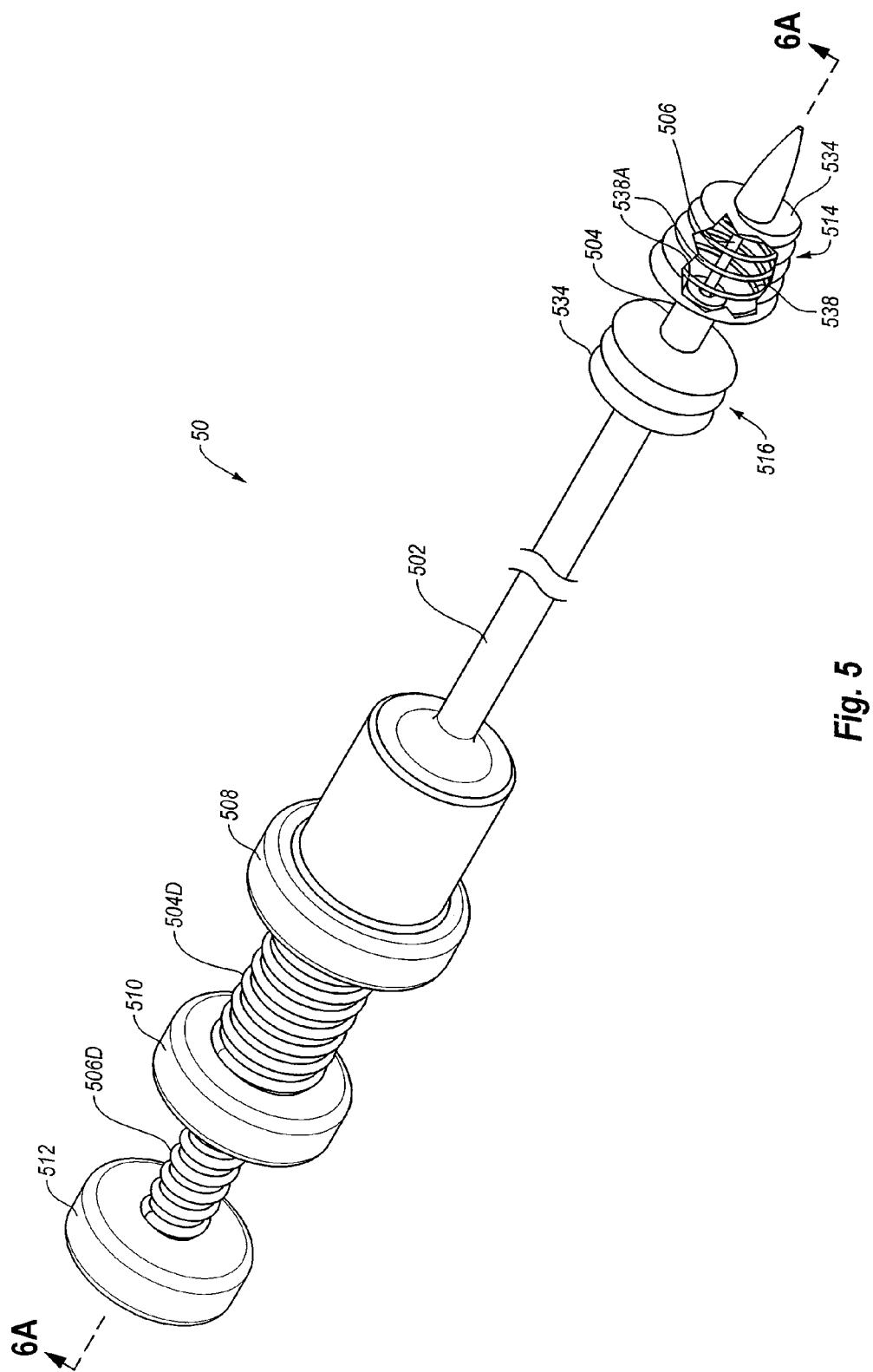
FIG. 5 illustrates a side perspective view of a device for penetrating thrombus according to an embodiment.

FIG. 5 illustrates a side perspective view of a device 50 for penetrating thrombus and/or recanalizing a vessel according to an embodiment. The device 50 may be similar in many respects to the device 10 and device 30 previously describe in FIGS. 1-4E. To the extent features or components of this configuration function in a manner similar to that as described above, such disclosure is hereby incorporated into the following additional configuration. Like structures and/or components are given like reference numerals. Additionally, the device 50 may incorporate at least one component of the device 10 and/or the device 30 described in FIG. 1-4E.

As shown in FIG. 5, the device 50 may include an elongated body having an outer barrel 502, an intermediate shaft 504, an inner shaft 506, a distal handle 508, an intermediate handle 510, a proximal handle 512, a first dynamic member 514, a second dynamic member 516, and a penetrating tip 518.

The outer barrel 502, the intermediate shaft 504, and the inner shaft 506 may have elongate flexible tubular bodies and be configured to move both axially and rotationally relative to each other. As shown, the inner shaft 506 may include outer threaded portion 506D having male thread, the proximal handle 512, and the penetrating tip 518. The inner shaft 506 may include a larger diameter proximal portion relative to a distal portion of the inner shaft 506. The proximal handle 512 may concentrically surround at least a portion of the inner shaft 506 and have a ring-like configuration. The proximal handle 512 may be integrally formed on the inner shaft 506 or affixed to the inner shaft 506 by a suitable adhesive, welding, brazing, fasteners, soldering, or the like.

The intermediate shaft 504 may include an outer threaded portion 504D having male thread, and an inner threaded portion 504E (shown in FIG. 6A) having female thread. The outer threaded portion 506D of the inner shaft 506 may rotatably engage the inner threaded portion 504E (shown in FIG. 6A) of the intermediate shaft 504. The intermediate handle 510 may be connected to the intermediate shaft 504 and may concentrically surround a portion of the intermediate shaft 504. The intermediate handle 510 may have a ring-like configuration and be integrally formed on the intermediate shaft 504 or affixed to the intermediate shaft 504 by any suitable method. The intermediate shaft 504 may also include a larger diameter proximal portion relative to a distal portion of the intermediate shaft 504.

The outer barrel 502 may include an inner threaded portion 502E (shown in FIG. 6A) having female thread and the distal handle 508. The outer threaded portion 504D of the intermediate shaft 504 may rotatably engage the inner threaded portion 502E (shown in FIG. 6A) of the outer barrel 502. Similar to the inner shaft 506 and the intermediate shaft 504, the outer barrel 502 may include a larger diameter proximal portion relative to a distal portion of the outer barrel 502.

The connections between the first dynamic member 514 and the inner shaft 506 and the intermediate shaft 504 and between the second dynamic member 516 and the intermediate shaft 504 and the outer barrel 502 may include bearing rings or other rotatable features such that the first dynamic member 514 and the second dynamic member 516 may rotate relative to the inner shaft 506, the intermediate shaft 504, and/or the outer barrel 502.

Similar to the first dynamic member 114 and the second dynamic member 116, the first dynamic member 514 and the second dynamic member 516 may be configured to selectively support and/or facilitate movement of the device 50 through thrombus. In an embodiment, both the first dynamic member 514 and the second dynamic member 516 may be moveable between a penetrating position and an anchoring position. As shown in FIG. 5, the first dynamic member 514 and the second dynamic member 516 may be located between the outer barrel 502, the intermediate shaft 504, and the inner shaft 506 and may include casings 534 disposed over coil springs 538. The coil springs 538 may concentrically surround at least a portion of the inner shaft 506 and/or intermediate shaft 504 and may be structurally supportive. The coil springs 538 may be formed of metals, plastic, rubber (natural or synthetic), shape memory materials, any composites thereof, or other substantially supportive and durable material. Moreover, the coil springs 538 may be configured to have sufficient radial strength to selectively exert a predetermined force against the thrombus within a vessel. As illustrated in FIG. 5, the coil spring 538 of the first dynamic member 514 may include a plurality of coil segments 538A in a conical configuration extending between a larger proximal base portion and a distal smaller apex portion. Such a tapered configuration may allow the first dynamic member 514 to move more easily through the thrombus. The coil spring 538 of the second dynamic member 516 may include a plurality of coil segments 538A (shown in FIG. 6A) in a generally cylindrical configuration. The casings 534 may be made of any suitable stretchable, flexible, resilient, deformable or elastic medical grade material, such as silicone rubber or sponge, to conform or stretch to the configuration and size of the first dynamic member 514 and/or the second dynamic member 516. Optionally, the casings 534 may be omitted from the device 50 or may be attached to inner portions of the coil springs 538.

While the first dynamic member 514 and the second dynamic member 516 are shown as coil springs, the first dynamic member 514 and the second dynamic member 516 may have different or similar structures and may comprise accordion sections, wire cages, wire frames, inflatable membranes, or any other structure having sufficient radial strength to selectively exert a predetermined force against the thrombus within the vessel. In addition, the device 50 may include one, three, four, five, or any number of dynamic members.

Figure 6C:
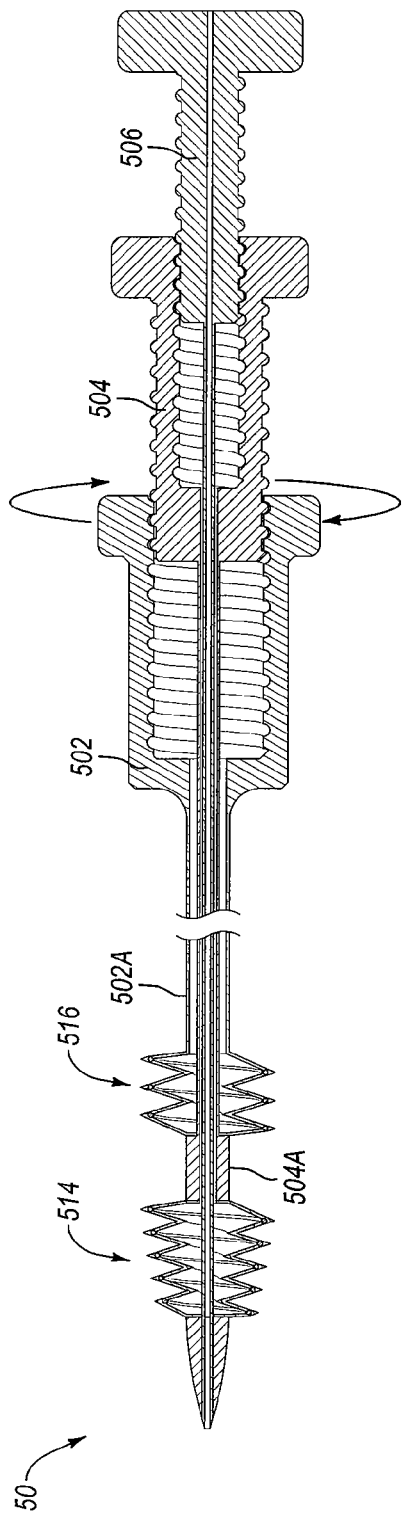

FIGS. 6A-6D illustrate cross-sectional views of the device of FIG. 5 taken along section line 6A-6A in various configurations. As shown in FIG. 6A, the inner threaded portion 502E of the outer barrel 502 may engage with the outer threaded portion 504D of the intermediate shaft 504. Similarly, the inner threaded portion 504E of the intermediate shaft 404 may engage with the outer threaded portion 506D of the inner shaft 506. In an embodiment, the first dynamic member 514 may move toward the penetrating position when the inner shaft 506 is threaded into the intermediate shaft 504. The second dynamic member 516 may move toward the penetrating position when the intermediate shaft 504 threaded into into the outer barrel 502. Referring still to FIG. 6A, the first dynamic member 514 and the second dynamic member 56 may include casings 534 disposed over coil springs 538. The coil springs 538 may include a plurality of coil segments 538A in a variety of configurations. In the penetrating position, the coil springs 538 may axially lengthen and radially contract. In the anchoring position, the coil springs 538 may axially contract and radially expand.

As shown in FIG. 6B, the first dynamic member 514 may move toward the anchoring position when the inner shaft 506 is unthreaded from the intermediate shaft 504. In the illustrated embodiment, the intermediate shaft 504 may be rotated in a first direction relative to the inner shaft 506 to axially move a distal portion 504A of the intermediate shaft 504 toward a distal portion 506A of the inner shaft 506. As a result, the intermediate shaft 504 moves the first dynamic member 114 into the anchoring position. In other embodiments, the inner shaft 506 may be rotated in a second direction relative to the intermediate shaft 506 to move the first dynamic member 514 toward the anchoring position.

As shown in FIG. 6C, the second dynamic member 516 may move toward the anchoring position when the intermediate shaft 504 is unthreaded from the outer barrel 502. In the illustrated embodiment, the outer barrel 502 may be rotated in a first direction relative to the intermediate shaft 504 to axially move a distal portion 502A of the outer barrel 502 toward the distal portion 504A of the intermediate shaft 504. As a result, the outer barrel 502 moves the second dynamic member 516 into the anchoring position. In other embodiments, the intermediate shaft 504 may be rotated in a second direction relative to the outer barrel 502 to move the second dynamic member 516 toward the anchoring position.

Figure 6D:
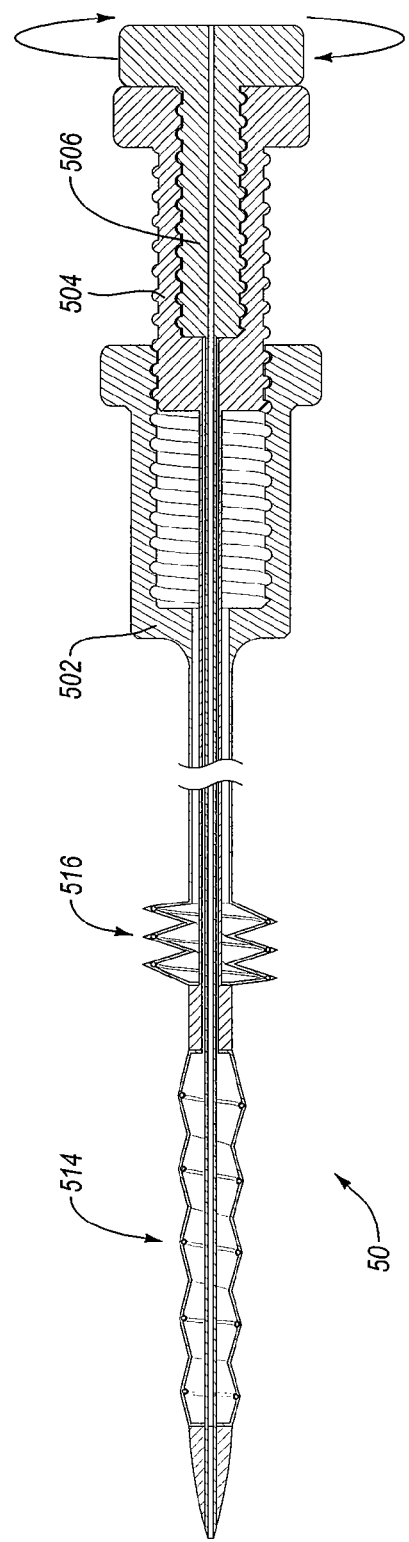

As shown in FIG. 6D, the first dynamic member 514 may also move from the anchoring position toward the penetrating position when the inner shaft 506 is threaded into the intermediate shaft 504. Referring again to FIG. 6A, the second dynamic member 516 may move from the anchoring position toward the penetrating position when the intermediate shaft 504 is threaded into the outer barrel 502.

As used herein "lead" may refer to the distance advanced parallel to a longitudinal axis of a threaded body (i.e., a screw or bolt) when the threaded body is turned one revolution. In an embodiment, the lead of the threaded portions of the outer barrel 502, the intermediate shaft 504, and/or the inner shaft 506 may be configured such that a specific number of revolutions can move the first dynamic member 514 and/or the second dynamic member 516 between the penetrating and anchoring positions. For example, in an embodiment, about four revolutions of the inner shaft 506 relative to the intermediate shaft 504 may move the first dynamic member 514 between a maximum penetrating position and a maximum anchoring position. In another embodiment, about seven revolutions of the outer barrel 502 relative to the intermediate shaft 504 may move the second dynamic member 516 between a maximum penetrating position and a maximum anchoring position. Accordingly, the amount of radial expansion and/or elongation of the first dynamic member 514 and/or the second dynamic members 516 may be gauged based on the number of revolutions of the inner shaft 506, the intermediate shaft 504, and/or the outer barrel 502.

Such a threaded configuration of the device 50 may provide a user substantial control over the movement of the first dynamic member 514 and the second dynamic member 516 between the penetrating and anchoring positions.

Embodiments of the dynamic members, outer barrel, inner and intermediate shafts, penetrating member, handles and the like may include a material made from any of a variety of known suitable biocompatible materials, such as a biocompatible shape memory material (SMM). SMMs have a shape memory effect in which they may be made to remember a particular shape. Once a shape has been remembered, the SMM may be bent out of shape or deformed and then returned to its original shape by unloading from strain or heating. Typically, SMMs may be shape memory alloys (SMA) comprised of metal alloys, or shape memory plastics (SMP) comprised of polymers. The materials may also be referred to as being superelastic.

Usually, an SMA may have an initial shape that may then be configured into a memory shape by heating the SMA and conforming the SMA into the desired memory shape. After the SMA is cooled, the desired memory shape may be retained. This allows for the SMA to be bent, straightened, twisted, compacted, and placed into various contortions by the application of requisite forces; however, after the forces are released, the SMA may be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios or by the conditions of manufacture. This may be used to tune the detachable needles so that it reverts to the memory shape to close the arteriotomy when deployed at body temperature and when being released from the tube set.

For example, the primary material of the dynamic members may be of a NiTi alloy that forms superelastic nitinol. Also, additional materials may be added to the nitinol depending on the desired characteristic. The alloy may be utilized having linear elastic properties or non-linear elastic properties.

An SMP is a shape-shifting plastic that may be fashioned into dynamic members, penetrating members, or other structures in accordance with the present disclosure. Also, it may be beneficial to include at least one layer of an SMA and at least one layer of an SMP to form a multilayered body; however, any appropriate combination of materials may be used to form a multilayered device. When an SMP encounters a temperature above the lowest melting point of the individual polymers, the blend makes a transition to a rubbery state. The elastic modulus may change more than two orders of magnitude across the transition temperature (Ttr). As such, an SMP may be formed into a desired shape of an endoprosthesis by heating it above the Ttr, fixing the SMP into the new shape, and cooling the material below Ttr. The SMP may then be arranged into a temporary shape by force and then resume the memory shape once the force has been released. Examples of SMPs include, but are not limited to, biodegradable polymers, such as oligo($\epsilon$-caprolactone)diol, oligo($\rho$-dioxanone) diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present disclosure.

The dynamic members, outer barrel, shafts, handles and the like may have at least one layer made of an SMM or suitable superelastic material. Also, the dynamic members, outer barrel, shafts, handles or other aspects or components of the penetrating device may be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/

0312740, which are each incorporated herein by reference, in their entireties) cobalt-chromium alloys, or other known biocompatible materials. Such biocompatible materials may include a suitable biocompatible polymer in addition to or in place of a suitable metal. The dynamic members may include biodegradable or bioabsorbable materials, which may be either plastically deformable or capable of being set in a anchoring configuration.

In one embodiment, the dynamic members, outer barrel, shafts, handles or other aspects or components of the penetrating device may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the dynamic members. The dynamic members have improved radiopacity yet retain their superelastic and shape memory behavior and further maintain a thin body thickness for high flexibility.

In one embodiment, the dynamic members, outer barrel, shafts, handles or other aspects or components of the penetrating device may be made at least in part of a high strength, low modulus metal alloy comprising Niobium, Tantalum, and at least one element selected from the group consisting of Zirconium, Tungsten, and Molybdenum.

In further embodiments, the dynamic members, outer barrel, shafts, handles or other aspects or components of the penetrating device may be made from or be coated with a biocompatible polymer. Examples of such biocompatible polymeric materials may include hydrophilic polymer, hydrophobic polymer biodegradable polymers, bioabsorbable polymers, and monomers thereof. Examples of such polymers may include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A device for penetrating occlusive material in a body lumen comprising:
   an outer tube;
   an intermediate tube, at least a portion of the intermediate tube being moveably disposed within the outer tube;
   an inner tube, at least a portion of the inner tube being moveably disposed within the intermediate tube, the inner tube including a penetrating member operatively connected with the inner tube;
   a first dynamic member operably connected to the intermediate tube and the inner tube, the first dynamic member being moveable between a first position in which the first dynamic member is substantially longitudinally elongated and configured to penetrate the occlusive material with the penetrating member and a second position in which the first dynamic member is substantially radially expanded and configured to anchor the first dynamic member within the occlusive material; and
   a second dynamic member operably connected with the intermediate tube and the outer tube, the second dynamic member being moveable between a first position in which the second dynamic member is substantially elongated and configured to penetrate the occlusive material and a second position in which the second dynamic member is substantially radially expanded and configured to anchor the second dynamic member within the occlusive material and to support movement of the first dynamic member;
   a proximal handle operatively connected to the first dynamic member, an intermediate handle operatively connected to the first dynamic member and the second dynamic member, and a distal handle operatively connected to the second dynamic member;
   wherein said first dynamic member is independently moveable relative to said second dynamic member with said second dynamic member in said second position, said second dynamic member being configured to resist distal longitudinal movement as said first dynamic member, in said first position, advances distally relative to said second dynamic member; and
   wherein the first dynamic member is moved into the second position when the distal and intermediate handles are distally separated from the proximal handle, and the second dynamic member is moved into the second position when the intermediate and proximal handles are separated proximally from the distal handle.

2. The device of claim 1, wherein the first dynamic member is moveable between the first position and the second position by relative movement of the intermediate tube and the inner tube relative to one another.

3. The device of claim 1, wherein the second dynamic member is moveable between the first position and the second position by relative movement of the intermediate tube and the outer tube relative to one another.

4. The device of claim 1, wherein the first dynamic member comprises an accordion-like structure having a plurality of segments pivotally connected at pivots, the plurality of segments concentrically surround at least a portion of the inner tube, wherein the plurality of segments are substantially rigid and configured to have a predetermined radial strength to selectively exert a force against the occlusive material when the first dynamic member is in the second position.

5. The device of claim 4, wherein a stretchable casing is disposed over the plurality of segments, the casing being configured to conform to the shape of the first dynamic member in the first position and the second position.

6. The device of claim 4 wherein the segments are pivoted relative to one another along the pivots to form a saw-tooth configuration with the pivots outwardly extending to form an enlargement when the first dynamic member is in the second position.

7. The device of claim 4, wherein the segments are substantially parallel with the inner tube when the first dynamic member is in the first position.

8. The device of claim 1, wherein the first dynamic member is rotatably connected to the inner tube and the intermediate tube, and wherein the first dynamic member is configured to rotate relative to the inner tube and the intermediate tube.

9. The device of claim 1, wherein the penetrating member comprises a generally conical shape with a rounded tip.

10. The device of claim 1, wherein the penetrating member includes a heating element configured to selectively heat the occlusive material.

11. The device of claim 1, wherein the inner tube is configured to move radially and axially relative to the intermediate tube, and wherein the intermediate tube is configured to move radially and axially relative to the outer tube.

12. The device of claim 1, wherein the first dynamic member in the second position is further configured to support movement of the second dynamic member.

13. A device for penetrating occlusive material in a body lumen comprising:
an outer tube;
an intermediate tube, at least a portion of the intermediate tube being moveably disposed within the outer tube;
an inner tube, at least a portion of the inner tube being moveably disposed within the intermediate tube;
a penetrating member operably connected with the inner tube and configured to penetrate the occlusive material;
a first dynamic member operably connected to the intermediate tube and the inner tube, the first dynamic member being moveable between a first position in which the first dynamic member is longitudinally elongated and radially contracted and a second position in which the first dynamic member is longitudinally truncated and radially expanded, said first dynamic member being configured to disengage from the body lumen and advance the penetrating member toward the occlusive material in said first position and said first dynamic member being configured to engage with the body lumen and resist longitudinal movement in said second position; and
a second dynamic member operably connected with the intermediate tube and the outer tube, the second dynamic member being moveable between a first position in which the second dynamic member is substantially elongated and radially contracted and a second position in which the second dynamic member is substantially radially expanded and longitudinally truncated, said second dynamic member being configured to disengage from the body lumen and advance toward said first dynamic member in said first position, and said second dynamic member being configured to engage with the body lumen and resist longitudinal movement of said second dynamic member in said second position;
a proximal handle operatively connected to the first dynamic member, an intermediate handle operatively connected to the first dynamic member and the second dynamic member, and a distal handle operatively connected to the second dynamic member;
wherein, said first dynamic member is configured to advance distally in said first position relative to said second dynamic member with said second dynamic member in said second position; and
wherein the first and second dynamic members are in the first position when the proximal, intermediate, and distal handles are positioned together, the first dynamic member is moved into the second position when the distal and intermediate handles are distally separated from the proximal handle, the second dynamic member is moved into the second position when the intermediate and proximal handles are separated proximally from the distal handle, and the first and second dynamic members are moved into the second position when the proximal, intermediate, and distal handles are positioned apart.

14. The device of claim 13, wherein the first dynamic member comprises an accordion-like structure having a plurality of segments pivotally connected at joints.

15. The device of claim 14, wherein a stretchable casing is disposed over the plurality of segments, the casing being configured to conform to the shape of the first dynamic member in the first position and the second position.

16. The device of claim 14 wherein the segments are pivoted relative to one another along the joints to form a sawtooth configuration with the joints outwardly extending to form an enlargement when the first dynamic member is in the second position.

17. The device of claim 14, wherein the penetrating member includes a heating element configured to selectively heat the occlusive material.

18. A device for penetrating occlusive material in a body lumen comprising:
an outer tube;
an intermediate tube, a portion of the intermediate tube being moveably disposed within the outer tube;
an inner tube, a portion of the inner tube being moveably disposed within the intermediate tube;
a penetrating member operably connected with the inner tube;
a first dynamic member operably connected to the intermediate tube and the inner tube, the first dynamic member being moveable between a first position in which the first dynamic member is longitudinally elongated and radially contracted and a second position in which the first dynamic member is longitudinally truncated and radially expanded; and
a second dynamic member operably connected with the intermediate tube and the outer tube, the second dynamic member being proximal the first dynamic member and being moveable between a first position in which the second dynamic member is substantially elongated and radially contracted and a second position in which the second dynamic member is substantially radially expanded and longitudinally truncated;
a distal handle operatively connected to the second dynamic member, an intermediate handle threaded into the distal handle and operatively connected to the first dynamic member and the second dynamic member, and a proximal handle threaded into the intermediate handle and operatively connected to the first dynamic member;
wherein, the first dynamic member and a distal portion of the inner tube and are configured to advance distally relative to the second dynamic member with the second dynamic member in the second position; and
wherein the first dynamic member is moved into the second position when the proximal handle is threaded out of the intermediate handle, and the second dynamic member is moved into the second position when the intermediate and proximal handles are threaded out of the distal handle.

19. The device of claim 18, wherein the first dynamic member comprises an accordion-like structure having a plurality of pivotally connected segments, the plurality of segments concentrically surround at least a portion of the inner tube, wherein the plurality of segments are substantially rigid and configured to have a predetermined radial strength to selectively exert a force against the occlusive material when the first dynamic member is in the second position.

20. The device of claim 19, wherein a stretchable casing is disposed over the plurality of segments.

21. The device of claim 19 wherein the plurality of segments form a saw-tooth configuration in the second position.

22. The device of claim 19, wherein the plurality of segments are substantially parallel with the inner tube when the first dynamic member is in the first position.

* * * * *